United States Patent
Pellevoisin et al.

(10) Patent No.: US 10,920,184 B2
(45) Date of Patent: Feb. 16, 2021

(54) MEMBRANE FOR RECONSTRUCTED TISSUE COMPRISING PORES OF SEVERAL DIAMETERS

(71) Applicant: L'OREAL, Paris (FR)

(72) Inventors: Christian Pellevoisin, Clichy (FR); Florent Sahuc, Lyons (FR)

(73) Assignee: L'OREAL, Paris (FR)

( * ) Notice: Subject to any disclaimer, the term of this patent is extended or adjusted under 35 U.S.C. 154(b) by 347 days.

(21) Appl. No.: 16/061,139

(22) PCT Filed: Dec. 19, 2016

(86) PCT No.: PCT/EP2016/081797
§ 371 (c)(1),
(2) Date: Jun. 11, 2018

(87) PCT Pub. No.: WO2017/103279
PCT Pub. Date: Jun. 22, 2017

(65) Prior Publication Data
US 2018/0362912 A1 Dec. 20, 2018

(30) Foreign Application Priority Data
Dec. 17, 2015 (FR) ...................................... 15 62707

(51) Int. Cl.
*C12N 5/00* (2006.01)
*C12M 3/00* (2006.01)
*C12M 1/12* (2006.01)
*G01N 33/50* (2006.01)
*C12M 1/32* (2006.01)

(52) U.S. Cl.
CPC ............ *C12M 25/14* (2013.01); *C12M 21/08* (2013.01); *C12M 25/02* (2013.01); *C12N 5/0068* (2013.01); *G01N 33/5029* (2013.01); *G01N 33/5047* (2013.01); *G01N 33/5082* (2013.01); *C12M 23/12* (2013.01); *C12N 2535/00* (2013.01); *G01N 2800/7095* (2013.01)

(58) Field of Classification Search
None
See application file for complete search history.

(56) References Cited

U.S. PATENT DOCUMENTS

| 2007/0264682 A1 | 11/2007 | Besne |
| 2007/0276507 A1* | 11/2007 | Bertram ................. A61F 2/042 623/23.65 |
| 2008/0044637 A1 | 2/2008 | Masuda et al. |
| 2010/0196444 A1 | 8/2010 | Dahlquist et al. |
| 2013/0143254 A1 | 6/2013 | Thomas et al. |
| 2014/0046236 A1 | 2/2014 | Filee et al. |
| 2014/0127744 A1 | 5/2014 | Schroeder et al. |
| 2014/0243354 A1 | 8/2014 | Chantalat et al. |

FOREIGN PATENT DOCUMENTS

| EP | 2 238 447 B1 | 2/2015 |
| JP | 2018 531519 A | 10/2018 |
| WO | WO 2005079985 A1 | 9/2005 |
| WO | WO 2007076061 A1 | 5/2007 |

OTHER PUBLICATIONS

He et al, Stroke, 2014, vol. 45, pp. 2514-2526. (Year: 2014).*
Greiner et al., "Multifunctional polymer scaffolds with adjustable pore size and chemoattractant gradients for studying cell matrix invasion", Biomaterials 35 (2014) 611-619.
Poumay et al., "A simple reconstructed human epidermis: preparation of the culture model and utilization in in vitro studies" Arch Dermatol Res (2004) 296: 203-211.
Corning—Transwell® Permable Supports Selection and Use Guide (2013), Retrieved from the Internet: URL:http://csmedia2.corning.com/LifeSciences/Media/pdf/transwellguide.pdf [retrieved on May 11, 2016].
Mori et al., "New model for studying the migration of immune cells into intestinal epithelial cell monolayers", Cytotechnology 43: 57-64 (2003).

\* cited by examiner

*Primary Examiner* — Allison M Fox
(74) *Attorney, Agent, or Firm* — Polsinelli PC

(57) ABSTRACT

The present invention relates to membranes comprising at least two types of porosity: —a porosity of small size but of high density, allowing for the support and nutrition of culture cells in such a way as to obtain a reconstructed tissue model, and—a porosity of large size but of low density, allowing for the circulation of some cell types and the passage of cytoplasmic extensions from one compartment to another.

14 Claims, 2 Drawing Sheets

MEMBRANE FOR RECONSTRUCTED TISSUE COMPRISING PORES OF SEVERAL DIAMETERS

CROSS REFERENCE TO RELATED APPLICATIONS

This application is the National Phase of Application No. PCT/EP2016/081797 filed Dec. 19, 2016, which claims priority to Application No. 15 62707 filed in France on Dec. 17, 2015 under 35 U.S.C. § 119. The entire contents of each application are hereby incorporated by reference.

The present invention relates to membranes and devices for cell culture adapted for the preparation of reconstructed biological tissue.

Tissue engineering for application in research, in particular in safety or efficacy tests, is based on reconstructing human or animal tissue containing one or more cell types. These tissues are most often reconstructed in inserts or devices for cell culture after seeding and culture in a medium and under defined conditions (adapted composition of the medium, controlled temperature and pH conditions).

Today these 3D tissue reconstruction systems use membranes that are used as a support for the deposit of cells. Due to the limitations inherent with the manufacturing technique thereof, in particular for membranes made of polycarbonate and other chemical polymers, all of the membranes of the market are proposed with only one pore diameter.

Therefore, most of the membranes used for 3D tissue reconstruction systems use membranes that have pores of a single diameter defined to allow for the diffusion of the nutritive medium from the lower compartment to the upper compartment.

Moreover, there are membranes that have pores of a single diameter defined to allow for the migration of cells from one compartment to another in cell migration assays. However, this single size of pores is not compatible with the reconstruction of a tissue model, such as a reconstructed human epidermis model.

However, there are many applications of reconstructed human or animal tissue models in which the circulation of cells between the lower and upper compartment of the culture device or the passage of cytoplasmic extensions between the different compartments may be very useful.

Therefore, the reconstructed human epidermis (RHE) models used in the study of inflammatory mechanisms are not representative of most inflammatory dermatosis (atopic dermatitis, psoriasis, lupus . . . ) as they are limited by the absence of lymphocyte cells. There is therefore a need for models that are better suited for the study of chronic inflammation, in particular a model authorizing the colonization of a reconstructed epithelium by cells involved in the inflammatory response of the organism.

Likewise, in some reconstructed animal or human epitheliums, incorporating several cell types of which immunocompetent cells, such as Langerhans cells, it would be interesting to be able to reproduce the activation of these cells and their migration outside of the epidermis as it happens in vivo in sensitization mechanisms.

Finally, human or animal epitheliums rarely contain the cell body of nerve cells but are often innervated by nerve endings. It would therefore be interesting to have 3D epithelium reconstruction models innervated by dendrites of which the cell bodies are located in a separate compartment.

There is therefore a substantial need for cell culture devices that allow for the preparation of a reconstructed tissue model in which the circulation of cells or the passage of cytoplasmic extensions between the different compartments is possible.

The present invention meets this need.

The present inventors have indeed surprisingly shown that it was possible to manufacture membranes comprising two types of porosity:

a porosity of small size but of high density, allowing for the support and nutrition of culture cells in such a way as to obtain a reconstructed tissue model, and a porosity of large size but of low density, allowing for the circulation of some cell types and the passage of cytoplasmic extensions from one compartment to another.

The inventors have shown that such membranes were perfectly suited for obtaining reconstructed tissue models in which the circulation of cells or the passage of cytoplasmic extensions between the various compartments is possible.

The present invention therefore has for object a monolayer membrane for cell culture comprising at least two types of pores:

(i) pores having an average diameter between 0.1 and 1 μm, at a density of $1 \times 10^5$ to $1 \times 10^8$ pores per $cm^2$ of membrane, and (ii) pores having an average diameter between 2 and 12 at, with a density of $0.5 \times 10^2$ to $5 \times 10^3$ pores per $cm^2$ of membrane, with the two types of pores crossing through the thickness of the membrane from one side to the other.

The pores (i) having an average diameter between 0.1 and 1 μm typically allow for the diffusion of the nutritive medium from one side of the membrane to the other.

Preferably, the pores (i) have an average diameter between 0.2 and 0.9 μm, preferably between 0.3 and 0.8 μm, preferably between 0.4 and 0.7 μm, between 0.4 and 0.6 μm or between 0.4 and 0.5 μm. Most preferably, the pores (i) have an average diameter of 0.4 μm.

Preferably, the pores (i) are present in the membrane according to the invention at a density between $2 \times 10^5$ and $9.5 \times 10^7$ pores per $cm^2$ of membrane, preferably between $3 \times 10^5$ and $9 \times 10^7$, between $4 \times 10^5$ and $8.5 \times 10^7$, between $5 \times 10^5$ and $8 \times 10^7$, between $6 \times 10^5$ and $7.5 \times 10^7$, between $7 \times 10^5$ and $7 \times 10^7$, between $8 \times 10^5$ and $6.5 \times 10^7$, between $9 \times 10^5$ and $6 \times 10^7$, between $1 \times 10^6$ and $5.5 \times 10^7$, between $2 \times 10^6$ and $5 \times 10^7$, between $3 \times 10^6$ and $4 \times 10^7$, between $4 \times 10^6$ and $3 \times 10^7$, between $5 \times 10^6$ and $2 \times 10^7$ or between $6 \times 10^6$ and $1 \times 10^7$ pores per $cm^2$ of membrane. Most preferably, the pores (i) are present in the membrane according to the invention at a density between $1 \times 10^6$ and $8.5 \times 10^7$ pores per $cm^2$ of membrane.

The pores (ii) having an average diameter between 2 and 12 μm typically allow for the migration of cells, in particular immune cells, or the passage of cell extensions, in particular nerve extensions, through the membrane.

Preferably, the pores (ii) have an average diameter between 2.5 and 11 μm, preferably between 3 and 10 μm, between 3.5 and 9 μm, between 4 and 8 μm, between 4.5 and 7 μm or between 5 and 6 μm. Most preferably, the pores (ii) have an average diameter of 5 μm.

The preferred average diameter of the pores (ii) can be chosen by those skilled in the art according to the type of cells for which the migration through the membrane is sought. For example, when the cells for which the migration is sought are astrocytes, the average diameter of the pores (ii) will preferably be 12 μm. When the cells for which the migration is sought are leukocytes, neutrophils and/or neuronal cells, the average diameter of the pores (ii) will preferably be 3 µm. When the cells for which the migration is sought are lymphocytes, macrophages, monocytes and/or dendritic cells, the average diameter of the pores (ii) will preferably be 5 µm. When the cells for which the migration is sought are endothelial cells, epithelial cells and/or fibroblasts, the average diameter of the pores (ii) will preferably be 8 µm.

Preferably, the pores (ii) are present in the membrane according to the invention at a density between $1 \times 10^2$ and $4.5 \times 10^3$ pores per $cm^2$ of membrane, preferably between $1.25 \times 10^2$ and $4 \times 10^3$, between $1.5 \times 10^2$ and $3 \times 10^3$, between $1.75 \times 10^2$ and $2 \times 10^3$, between $2 \times 10^2$ and $1.5 \times 10^3$, between $2.25 \times 10^2$ and $1 \times 10^3$, between $2.5 \times 10^2$ and $9.5 \times 10^2$, between $2.75 \times 10^2$ and $9 \times 10^2$, between $3 \times 10^2$ and $8.5 \times 10^2$, between $3.25 \times 10^2$ and $8 \times 10^2$, between $3.5 \times 10^2$ and $7.5 \times 10^2$, between $3.75 \times 10^2$ and $7 \times 10^2$, between $4 \times 10^2$ and $6.5 \times 10^2$, between $4.25 \times 10^2$ and $6 \times 10^2$, between $4.5 \times 10^2$ and $5.75 \times 10^2$, between $4.75 \times 10^2$ and $5.5 \times 10^2$ or between $5 \times 10^2$ and $5.25 \times 10^2$ pores per $cm^2$ of membrane. Most preferably, the pores (ii) are present in the membrane according to the invention at a density between $2.5 \times 10^2$, $5 \times 10^2$ or $1 \times 10^3$ pores per $cm^2$ of membrane.

In a particular embodiment, the pores (ii) are distributed homogeneously over the entire surface of the membrane.

In another particular embodiment, the pores (ii) are distributed heterogeneously over the surface of the membrane.

Preferably, the two types of (i) and (ii) are oriented in the same direction.

In a particularly preferred embodiment, the membrane according to the invention is a monolayer membrane for cell culture comprising at least two types of pores:

(i) pores having an average diameter of 0.4 µm, at a density of $1 \times 10^6$ to $8.5 \times 10^7$ pores per $cm^2$ of membrane, and (ii) pores having an average diameter between 2 and 12 µm, preferable 5 µm, at a density of $2.5 \times 10^2$ to $1 \times 10^3$ pores per $cm^2$ of membrane, preferably a density of $2.5 \times 10^2$, $5 \times 10^2$ or $1 \times 10^3$ per $cm^2$ of membrane, with the two types of pores crossing through the thickness of the membrane from one side to the other and being oriented in the same direction.

The pores (i) and (ii) of the membrane according to the invention cross through the thickness of the membrane. They therefore create passageways between elements located on one side of the membrane and elements located on the other side of the membrane.

The pores (i) and (ii) of the membrane according to the invention are moreover preferably oriented in the same direction. Consequently, the pores (i) and (ii) of the membrane according to the invention preferably form passageways that are substantially parallel with respect to one another. Accordingly, preferably, the pores (i) and (ii) of the membrane according to the invention are not interconnected.

The membrane according to the invention is a monolayer membrane. In other words, the membrane according to the invention is constituted of a single layer or sheet of material.

Preferably, the membrane according to the invention has a thickness between 2 µm and 200 µm. More preferably, the membrane according to the invention has a thickness between 5 µm and 100 µm, preferably between 5 and 50 µm, preferably between 8 and 25 µm, more preferably between 10 µm and 20 µm, most preferably between 11 µm and 15 µm.

The membrane according to the invention is preferably a biocompatible membrane.

The term "biocompatible membrane" here means a membrane that is made of a material that does not have a deleterious effect on the cells, in particular on the viability, adhesion, spreading, mobility, growth and/or division of cells.

The membrane can be a semi-permeable membrane of polycarbonate, polyethylene, polypropylene, polyethylene terephtalate (PET) or polyester. Preferably, the membrane according to the invention is a polycarbonate membrane.

The membrane according to the invention can further be covered with a coating in order to promote cell adhesion.

The coating can comprise biomolecules or derivatives of biomolecules, such as a polymer such as polyornithine or polylysine, peptides or proteins, or extracellular matrix components, such as gelatin, fibronectin, laminin, collagen, a glycosaminoglycan, a peptidoglycan, etc.

The coating preferably covers the entire surface of the membrane in contact with the cells.

The coating can be in semi-solid or gel form, and can comprise additional components, such as growth factors. The coating can be a simple or complex mixture of biomolecules and can simulate or be the replica of a natural extracellular matrix (ECM). In particular, the coating can be the Matrigel™ matrix sold by BD Biosciences.

The inventors have furthermore shown that the membrane according to the invention can be obtained surprisingly by perforation, in particular with a laser, of a cell culture membrane that has only a porosity of small size but at a high density, in such a way as to produce pores that have a higher diameter but at a low density.

The present invention therefore also relates to a method for manufacturing a membrane as defined hereinabove, comprising the step consisting in perforating a monolayer membrane for cell culture, comprising pores having an average diameter between 0.1 and 1 µm, at a density of $1 \times 10^5$ to $1 \times 10^8$ pores per $cm^2$ of membrane, in such a way as to produce pores that have an average diameter between 2 and 12 µm, at a density of $0.5 \times 10^2$ to $5 \times 10^3$ pores per $cm^2$ of membrane.

Preferably, the method of manufacture according to the invention comprises the following steps:

(a) providing a monolayer membrane for cell culture comprising pores having an average diameter between 0.1 and 1 µm, at a density of $1 \times 10^5$ to $1 \times 10^8$ pores per $cm^2$ of membrane, and (b) perforating said membrane in such a way as to produce pores having an average diameter between 2 and 12 µm, at a density of $0.5 \times 10^2$ to $5 \times 10^3$ pores per $cm^2$ of membrane.

Preferably, the pores already present in the membrane which is subjected to the step of perforating, in particular the pores of the membrane provided in step a), have an average diameter between 0.2 and 0.9 µm, preferably between 0.3 and 0.8 µm, preferably between 0.4 and 0.7 µm, between 0.4 and 0.6 µm or between 0.4 and 0.5 µm. Most preferably, the pores already present in the membrane which is subjected to the step of perforating, in particular the pores of the membrane provided in step a), have an average diameter of 0.4 µm.

Preferably, the pores already present in the membrane which is subjected to the step of perforating, in particular the pores of the membrane provided in step a), are present in the membrane at a density between $2 \times 10^5$ and $9.5 \times 10^7$ pores per $cm^2$ of membrane, preferably between $3 \times 10^5$ and $9 \times 10^7$, between $4 \times 10^5$ and $8.5 \times 10^7$, between $5 \times 10^5$ and $8 \times 10^7$, between $6 \times 10^5$ and $7.5 \times 10^7$, between $7 \times 10^5$ and $7 \times 10^7$, between $8 \times 10^5$ and $6.5 \times 10^7$, between $9 \times 10^5$ and $6 \times 10^7$, between $1 \times 10^6$ and $5.5 \times 10^7$, between $2 \times 10^6$ and $5 \times 10^7$, between $3 \times 10^6$ and $4 \times 10^7$, between $4 \times 10^6$ and $3 \times 10^7$, between $5 \times 10^6$ and $2 \times 10^7$ or between $6 \times 10^6$ and $1 \times 10^7$ pores per cm$^2$ of membrane. Most preferably, the pores already present in the membrane which is subjected to the step of perforating, in particular the pores of the membrane provided in step a), are present in the membrane at a density between 1×10$^6$ and 8.5×10$^7$ pores per cm$^2$ of membrane.

In a particularly preferred embodiment, the membrane which is subjected to the step of perforating, in particular the membrane provided in step a), is a monolayer membrane for cell culture comprising pores having an average diameter of 0.4 µm, at a density of 1×10$^6$ to 8.5×10$^7$ pores per cm$^2$ of membrane.

Preferably, the pores already present in the membrane which is subjected to the step of perforating, in particular the pores of the membrane provided in step a), cross through the thickness of the membrane from one side to the other.

The membrane which is subjected to the step of perforating, in particular the membrane provided in step a), is a monolayer membrane. In other words, the membrane which is subjected to the step of perforating, in particular the membrane provided in step a), is constituted of a single layer of sheet of material.

Preferably, the membrane which is subjected to the step of perforating, in particular the membrane provided in step a), has a thickness between 2 µm and 200 µm. More preferably, the membrane which is subjected to the step of perforating, in particular the membrane provided in step a), has a thickness between 5 µm and 100 µm, preferably between 5 and 50 µm, preferably between 8 and 25 µm, more preferably between 10 µm and 20 µm, most preferably between 11 µm and 15 µm.

The membrane which is subjected to the step of perforating, in particular the membrane provided in step a), is preferably a biocompatible membrane, as defined hereinabove.

The membrane which is subjected to the step of perforating, in particular the membrane provided in step a), can be a semi-permeable membrane of polycarbonate, polyethylene, polypropylene, polyethylene terephtalate (PET) or polyester. Preferably, the membrane which is subjected to the step of perforating, in particular the membrane provided in step a), is a polycarbonate membrane.

The membrane which is subjected to the step of perforating, in particular the membrane provided in step a), can further be covered with a coating in order to promote cell adhesion, as defined hereinabove.

Preferably, the membrane is perforated by laser perforation.

The terms "perforation with a laser", "laser perforation", or "perforate with a laser" here mean the action of piercing an object by means of a laser. The techniques of laser perforation are well known to those skilled in the art and are for example described in Mielke et al. (2013) *JLMN-Journal of Laser Micro/Nanoengineering* 8:115-123.

A laser of the femtosecond type that produces ultra-short pulses, the duration of which is of about a few femtoseconds to a few hundred femtoseconds can be used.

Preferably, the perforation with a laser implemented in the method for manufacture according to the invention is a microperforation with a laser, more preferably a femtosecond laser microperforation.

Typically, the perforation with a laser is implemented using a femtosecond laser, preferably with a single Bessel beam pulse, preferably of about a hundred nanojoules per hole.

The pores formed at the step of perforation in the method of manufacture according to the invention allow for the migration of cells or the passage of cell extensions through the membrane.

Preferably, the pores formed at the step of perforating have an average diameter between 2.5 and 11 µm, preferably between 3 and 10 µm, between 3.5 and 9 µm, between 4 and 8 µm, between 4.5 and 7 µm or between 5 and 6 µm. Most preferably, the pores formed at the step of perforating have an average diameter of 5 µm.

The average diameter of the pores formed at the step of perforating can be chosen by those skilled in the art according to the type of cells for which the migration through the membrane is sought, as indicated hereinabove.

Preferably, the pores formed at the step of perforating are perforated in the membrane in particular provided in step a) at a density between 1×10$^2$ and 4.5×10$^3$ pores per cm$^2$ of membrane, preferably between 1.25×10$^2$ and 4×10$^3$, between 1.5×10$^2$ and 3×10$^3$, between 1.75×10$^2$ and 2×10$^3$, between 2×10$^2$ and 1.5×10$^3$, between 2.25×10$^2$ and 1×10$^3$, between 2.5×10$^2$ and 9.5×10$^2$, between 2.75×10$^2$ and 9×10$^2$, between 3×10$^2$ and 8.5×10$^2$, between 3.25×10$^2$ and 8×10$^2$, between 3.5×10$^2$ and 7.5×10$^2$, between 3.75×10$^2$ and 7×10$^2$, between 4×10$^2$ and 6.5×10$^2$, between 4.25×10$^2$ and 6×10$^2$, between 4.5×10$^2$ and 5.75×10$^2$, between 4.75×10$^2$ and 5.5×10$^2$ or between 5×10$^2$ and 5.25×10$^2$ pores per cm$^2$ of membrane. Most preferably, the pores formed in step b) are perforated in the membrane provided in step a) with a density between 2.5×10$^2$, 5×10$^2$ or 1×10$^3$ pores per cm$^2$ of membrane.

In a particularly preferred embodiment, the step of perforating consists in perforating with a laser the membrane in particular provided in step a) in such a way as to produce pores having an average diameter between 3 and 8 µm, preferable 5 µm, at a density of 2.5×10$^2$ to 1×10$^3$ pores per cm$^2$ of membrane, preferably a density of 2.5×10$^2$, 5×10$^2$ or 1×10$^3$ per cm$^2$ of membrane, Preferably, the pores formed in the step of perforating cross through the thickness of the membrane from one side to the other.

Preferably, the pores formed in the step of perforating are oriented in the same direction as the pores initially present in the membrane.

The membrane according to the invention is particularly useful for cell culture when it is part of a cell culture device.

This invention therefore also has for object a cell culture device comprising at least one compartment of which at least one of the walls comprises or is constituted by the membrane according to the invention.

The terms "cell culture device" and "insert" are used here indifferently.

The term "insert" here means a support that comprises one or more troughs or wells that can be placed in a container, typically in a multi-well culture plate.

Preferably, the cell culture device according to the invention comprises two compartments, with the wall comprising or being constituted by the membrane according to the invention separating the two compartments.

The base of the insert is preferably constituted by the membrane according to the invention which therefore separates the compartment formed by the well of the insert and a second compartment of the insert or the compartment formed by the container in which the insert is placed.

The insert can be of any shape and of any size. The insert can in particular have a diameter between 3 and 80 mm, between 4 and 75 mm, between 4.26 and 70 mm, between 4.5 and 65 mm, between 5 and 60 mm, between 5.5 and 55 mm, between 6 and 50 mm, between 6.5 and 45 mm, between 7 and 40 mm, between 7.5 and 35 mm, between 8 and 30 mm, between 8.5 and 25 mm, between 9 and 24 mm, between 9.5 and 23 mm, between 10 and 22 mm, between 11 and 21 mm, between 12 and 20 mm, between 13 and 19 mm, between 14 and 18 mm, between 15 and 17 mm or between 15 and 16 mm.

The insert can be arranged in such a way as to be positioned in a cell culture plate well without being in contact with the bottom of said well.

The insert can comprise lugs, hooks or any other means that allows it to be maintained at a suitable distance from the bottom of a cell culture plate well.

The present invention therefore also relates to a method for manufacturing a cell culture device according to the invention, comprising the step consisting in perforating the monolayer membrane of a cell culture device which comprises at least one compartment of which at least one of the walls comprises or is constituted by this monolayer membrane which comprises pores having an average diameter between 0.1 and 1 µm, at a density of $1 \times 10^5$ to $1 \times 10^8$ pores per cm² of membrane, in such a way as to produce pores that have an average diameter between 2 and 12 µm, at a density of $0.5 \times 10^2$ to $5 \times 10^3$ pores per cm² of membrane.

Preferably, the method of manufacturing a cell culture device according to the invention, comprises the following steps:
A) providing a cell culture device that comprises at least one compartment of which at least one of the walls comprises or is constituted by a monolayer membrane comprising pores having an average diameter between 0.1 and 1 µm, at a density of $1 \times 10^8$ to $1 \times 10^8$ pores per cm² of membrane, and
B) perforating said membrane in such a way as to produce pores having an average diameter between 2 and 12 µm, at a density of $0.5 \times 10^2$ to $5 \times 10^3$ pores per cm² of membrane.

The membrane of the cell culture device which is subjected to the step of perforating, in particular of the device provided in step A), is as defined hereinabove for the membrane which is subjected to the step of perforating, in particular the membrane provided in step a), of the method of manufacture of the membrane according to the invention.

Preferably, the cell culture device of which the membrane is subjected to the step of perforating, in particular the device provided in step A), comprises two compartments, with the wall comprising or being constituted by said membrane separating the two compartments.

The cell culture device of which the membrane is subjected to the step of perforating, in particular the device provided in step A), can typically be an insert available commercially such as an insert for cell culture of 0.5 cm² or 4 cm² of culture surface sold by Nunc, or an insert for cell culture of 0.38 cm² or 1.2 cm² of culture surface sold by Corning.

Preferably, the membrane is perforated by perforation with a laser.

The step of perforating can be implemented in the same conditions as those defined for the step of perforating of the method for manufacturing the membrane according to the invention, and for producing pores having the same features.

The inventors have shown that the membrane and the cell culture device according to the invention were particularly useful for cell culture, and in particular for producing reconstructed biological tissues towards which or from which cells can circulate.

The present invention therefore also has for object the in vitro use of the membrane according to the invention or of the cell culture device according to the invention for cell culture.

The present invention therefore also has for object the use of the membrane according to the invention or of the cell culture device according to the invention for the preparation of a reconstructed biological tissue.

The term "biological tissue" here means any set of similar cells and of the same origin, grouped into a cluster, network or beam. The biological tissue can in particular be an epithelial, conjunctive, muscle or nerve tissue. The biological tissue is preferably an epithelial tissue.

It may be a tissue from any human organ, such as epidermis tissue, dermis tissue, heart tissue, hepatic tissue, kidney tissue, etc.

The present invention thus also relates to a reconstructed biological tissue comprising, on the membrane according to the invention, at least one group of cells (i) comprising at least one first cell type.

Preferably, said membrane allows for the passage of certain cells and/or cytoplasmic extensions of certain cells of said biological tissue, in particular through the pores of a diameter between 2 and 12 µm.

Preferably, said at least one first cell type comprised in the group of cells (i) is constituted of epithelium cells.

The term "epithelium cells" here means any cell that is part of an epithelium.

The epithelium cells of the reconstructed biological tissue according to the invention can for example be cells of the epidermis, vaginal, oral, pulmonary, intestinal or corneal epithelium as well as all the cells which reside in these epithelial tissues. Thus, the group of cells (i) of the reconstructed biological tissue according to the invention can constitute an epidermis, vaginal, oral, pulmonary, intestinal or corneal epithelium equivalent.

The epithelium cells used in the context of the invention are preferably epithelial cells. Keratinocytes will preferentially be used.

The group of cells (i) can furthermore comprise other cell types than the first cell type, such as immune cells.

In a particular embodiment, said group of cells (i) further comprises immune cells.

The term "immune cells" here refers to any cell involved in the immune responses of an organism. Immune cells include in particular lymphocytes such as lymph node lymphocytes, leukocytes, macrophages, monocytes, dendritic cells and Langerhans cells.

In a preferred embodiment of the invention, the reconstructed biological tissue according to the invention comprises:
a group of cells (i) comprising at least one first cell type, as defined hereinabove, and
a group of cells (ii) comprising at least one second cell type,
with the groups of cells (i) and (ii) being separated by the membrane according to the invention.

Preferably, said at least one second cell type comprised in the group of cells (ii) is constituted of nerve cells.

The term "nerve cells" refers here to any cell involved in the nervous system, including glial cells. Nerve cells include in particular neurons, among which motoneurons, sensitive neurons and association neurons, astrocytes, oligodendrocytes and Schwann cells. Preferably, the nerve cell included in the reconstructed tissue according to the invention is a nerve cell with a cytoplasmic extension.

Therefore, in a preferred embodiment, said membrane allows for the passage of cytoplasmic extensions of the group of cells (ii) of said biological tissue to the group of cells (i), in particular through the pores of 2 to 12 μm in diameter.

In another preferred embodiment, said membrane allows for the passage of cytoplasmic extensions of nerve cells of the group of cells (ii) of said biological tissue to the group of cells (i), in particular through the pores of 2 to 12 μm in diameter.

In a particular embodiment, the reconstructed biological tissue according to the invention is a reconstructed skin model.

Therefore, in this particular embodiment, the group of cells (i) of the reconstructed biological tissue preferably constitutes an epidermis equivalent.

In this epidermis equivalent (i), said at least first cell type is constituted of epithelium cells, preferably epidermis cells, in particular cells chosen from the group consisting in keratinocytes, melanocytes and mixtures thereof.

Preferably, the epidermis equivalent (i) comprises immune cells, as defined hereinabove, in particular Langerhans cells and/or precursors of Langerhans cells.

Preferably, these Langerhans cells are located in the suprabasal portion of the epidermis equivalent (i).

The present invention also has for object a method for preparing a reconstructed biological tissue comprising at least one cell type, in a cell culture device according to the invention, comprising the following steps:

a) seeding a first cell type of the tissue to be reconstructed in a compartment of the culture device, in such a way as to allow for its adhesion to the membrane of the culture device, and b) maintaining the cells in culture for a period and in conditions suitable for enabling the characteristic cellular organization of the tissue.

In a particular embodiment, the method is for preparing a reconstructed biological tissue comprising at least two cell types, and comprises the following steps:

a1) seeding a first cell type of the tissue to be reconstructed in a compartment of the culture device, a2) after a period required to allow for the adhesion of the cells to the membrane of the culture device, seeding the second cell type, and b) maintaining the cells in culture for a period and in conditions suitable for enabling the characteristic cellular organization of the tissue.

Preferably, the first cell type of the tissue to be reconstructed is an epithelium cell as defined hereinabove.

In a particular embodiment, step a) or a1) of seeding the first cell type of the tissue to be reconstructed can include the seeding of several cell types, which will constitute a first set of reconstructed biological tissue. Therefore, in a particular embodiment, step a) or a1) of seeding the first cell type of the tissue to be reconstructed includes the simultaneous or consecutive seeding of several types of epithelium cells, preferably the simultaneous or consecutive seeding of keratinocytes and melanocytes. Step a) or a1) of seeding the first cell type of the tissue to be reconstructed can furthermore include the simultaneous or consecutive seeding of immune cells as defined hereinabove, in particular of Langerhans cells or of precursors of Langerhans cells.

Preferably, the second cell type of the tissue to be reconstructed is a nerve cell such as defined hereinabove or an immune cell such as defined hereinabove.

The seeded cells are maintained in culture in step b) for a period and in conditions suitable for enabling the characteristic cellular organization of the tissue, for example in an atmosphere of air containing 2 to 10% $CO_2$ at 37° C.

All of the cells of the reconstructed biological tissue according to the invention can be placed in a culture in a medium suitable for maintaining and/or for the growth and/or the proliferation of each one of the cell types of the tissue.

Many culture mediums likely to be suitable for implementing the invention can be obtained commercially. As examples of culture mediums that are suitable for the invention, mention can be made of Dulbecco's Modified Eagle's Medium (DMEM), MCDB 153 or other derivatives, Minimal Essential Medium (MEM), M199, RPMI 1640 or Iscove's Modified Dulbecco's Medium (EDMEM), Ham's F-12, Ham's F-10, NCTC 109 and NCTC 135.

These mediums can be supplemented with any additive that is conventionally used in cell culture such as, for example, precursors of phospholipides, non-essential amino acids, nucleic acids, vitamins, antibiotics, enzymatic co-factors, mineral salts, insulin, transferrin, triiodothyronine, ethanolamine, o-phosphoryl-ethanolamine or growth factors.

The concentrations of the various additives usually used for supplementing cell culture mediums can be determined and adapted by those skilled in the art, in particular according to the type of cells to be cultivated.

Moreover, it is also possible to use mixtures of various mediums in particular of the aforementioned mediums, such as for example a DMEM/Ham's F-12 mixture.

Generally, a reconstructed biological tissue according to the invention can be maintained in conditions of culture, of maintaining, or survival and/or of growth and/or of cell proliferation for a period of about 5 to 24 days, in standard culture conditions.

As indicated hereinabove, the use of a membrane suited for the obtaining of reconstructed tissue models and allowing for the circulation of cells is particularly suitable for implementing screening or identification assays of compounds likely to modulate an inflammatory or immune response of a human tissue such as for example an epithelium.

The use of a membrane suitable for the obtaining of reconstructed tissue models and allowing for the passage of cytoplasmic extensions is also particularly suitable for implementing screening or identification assays of compounds likely to modulate a sensory response of a human tissue by interacting with the nerve endings present in the tissue.

The present invention therefore also has for object the use of a reconstructed biological tissue according to the invention to screen or identify agents likely to modulate an inflammatory response of a biological tissue, in particular of an epithelium, involving the activation and the migration of immune cells or for screening agents likely to modulate a sensory response of a biological tissue by interacting with the nerve endings present in the tissue.

The present invention also has for object an in vitro method for screening agents likely to modulate an inflammatory response of a biological tissue, in particular of an epithelium, involving the activation and the migration of immune cells comprising the following steps:

a) placing the agent to be screened in the presence of a reconstructed biological tissue according to the invention displaying an inflammatory response involving the activation and the migration of immune cells in this reconstructed biological tissue, b) determining a possible change in the activation and the migration of immune cells in the reconstructed biological tissue, and c) if a change is determined in step b), deducing therefrom that the agent to be screened is an agent likely to modulate the inflammatory response of a tissue, in particular of an epithelium involving the activation and the migration of immune cells.

Preferably, in these embodiments, the membrane of the reconstructed biological tissue allows for the passing, in particular through the pores of a diameter between 2 and 12 µm, of immune cells, as defined hereinabove, from the reconstructed biological tissue to another compartment, and inversely.

Preferably, the reconstructed biological tissue displaying an inflammatory response that involves the activation and the migration of immune cells is a reconstructed skin model, as defined hereinabove, which is an inflammation model, in particular a reconstructed skin model as defined hereinabove colonized by cells involved in the inflammatory response, in particular immune cells such as lymphocytes, leukocytes, macrophages, monocytes, dendritic cells and Langerhans cells.

The present invention also has for object an in vitro method for screening agents likely to modulate a sensory response of a biological tissue, in particular of an epithelium, by interacting with nerve endings present in the tissue, comprising the following steps:

a) placing the agent to be screened in the presence of a reconstructed biological tissue according to the invention comprising a group of cells (i) comprising at least one first cell type, and a group of cells (ii) comprising nerve cells, with the groups of cells (i) and (ii) being separated by the membrane according to the invention which allows for the passing of cytoplasmic extensions of nerve cells of the group of cells (ii) to the group of cells (i), b) determining a possible change in the activity of the nerve cells in the reconstructed biological tissue, by measuring the electrical activity in the nerve cells and/or of the release of substance P by the nerve cells, and c) if a change is determined in step b), deducing therefrom that the agent to be screened is an agent likely to modulate the sensory response of a tissue, in particular of an epithelium, by interacting with the nerve endings present in the tissue.

The agent to be screened is preferably placed in the presence of the reconstructed biological tissue in conditions that favor an interaction with said tissue, in particular by contact with at least one of the cell types in culture and/or with at least one culture medium of said cells, in particular in an insert and/or a well.

This invention shall be illustrated in more detail by the figures and example hereinbelow.

EXAMPLES

Example 1: Manufacture of Membranes and Inserts According to the Invention

The inventors have shown that it was possible using industrial inserts of the market used for cell culture and tissue reconstruction to manufacture a system that has two different diameters of pores or more.

Figure 1:
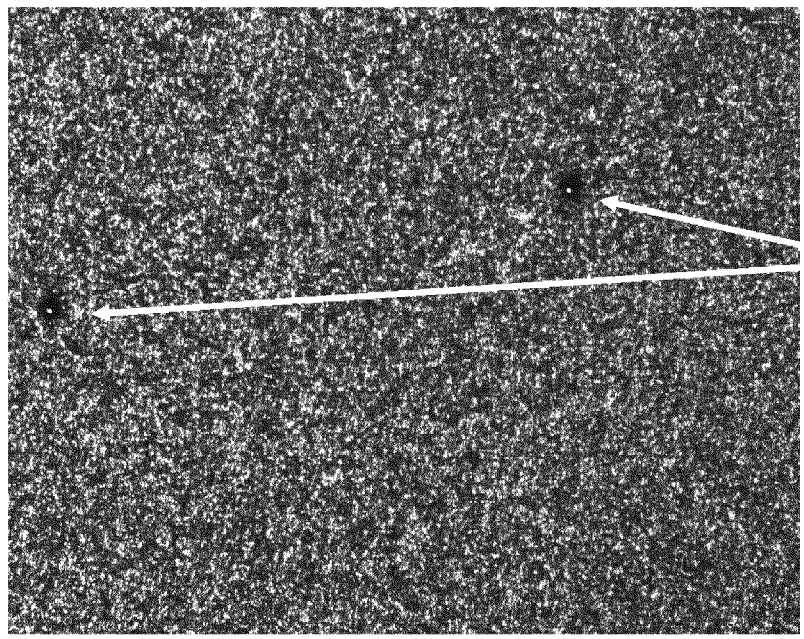
FIG. 1: Optical microscope photograph of the membrane of polycarbonate of a Nunc insert with a high density of pores of 0.4 µm in which has been added a low density of pores of 5 µm.

Nunc inserts (Cat No 140700) comprising a polycarbonate membrane of 0.5 cm$^2$ and of 11 µm in thickness, provided with pores of 0.4 µm with a density <0.85×10$^8$ pores/cm$^2$ were perforated by a laser perforation technique, in such a way as to produce pores of a diameter of 5 µm with a density of 250, 500 and 1000 pores per cm$^2$ (FIG. 1).

These pores are more precisely produced by using a femtosecond type laser with a single Bessel beam pulse of about a hundred nanojoules per hole.

Figure 2:
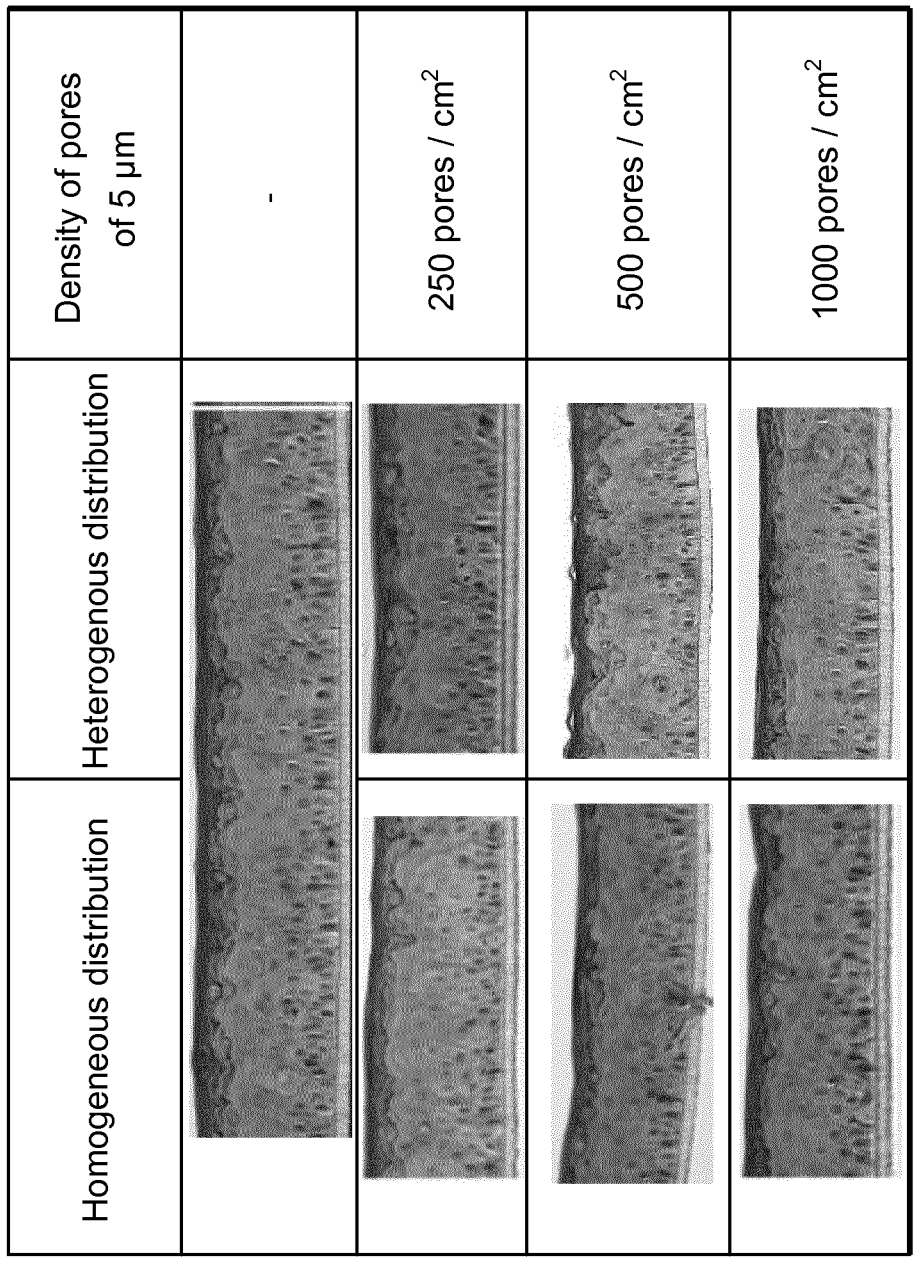
FIG. 2: Photograph of a histological section of reconstructed epidermis on a conventional membrane that only has a porosity of 0.4 µm or on membranes in which pores of 5 µm have been added.

Example 2: Reconstruction of a Tissue on the Membrane According to the Invention Using the conventional techniques for reconstructing human epithelium models, the inventors reconstructed on the membrane of example 1 a reconstructed human epidermis (RHE) having morphological (histology) and functional (cell viability, barrier function) characteristics equivalent to those of a standard RHE skinethic model (FIG. 2).

After seeding of the inserts by keratinocytes, the inserts were placed directly at the air-liquid interface and the reconstruction continued for 17 days without changing the medium.

The inventors used two types of membranes: membranes in which the pores of 5 µm in diameter are distributed homogeneously over the entire surface of the membrane, and membranes in which the pores of 5 µm in diameter are distributed heterogeneously over the membrane.

Several densities of pores of 5 µm in diameter were moreover tested: 250 pores per cm$^2$, 500 pores per cm$^2$ and 1000 pores per cm$^2$.

The RHE models obtained on these membranes were compared to the RHE models prepared on a standard membrane that only had pores of 0.4 µm in diameter.

The RHE models obtained on the membranes according to the invention have the same morphological characteristics of an epidermis (basal layer, spinous layer, grainy layer and stratum corneum) as an RHE model obtained on a standard membrane. However, they have the additional advantage of allowing the passage of cells and/or of cytoplasmic extensions through the membrane, a passage which is impossible with standard membranes The presence of pores of 5 µm in diameter in the polycarbonate membrane of this RHE model allows indeed for the passage, in this example, of cells from the lower compartment to the upper compartment in order to mimic the process of lymphocystic invasion such as those observed in certain inflammatory skin disorders.

The invention claimed is:

1. A monolayer membrane for cell culture comprising at least two types of pores:
   (i) pores having an average diameter between 0.1 and 1 µm, at a density of $1\times10^5$ to $1\times10^8$ pores per cm$^2$ of membrane, and
   (ii) pores having an average diameter between 2 and 12 µm, at a density of $0.5\times10^2$ to $5\times10^3$ pores per cm$^2$ of membrane, with the two types of pores crossing through the thickness of the membrane from one side to the other.

2. The monolayer membrane according to claim 1, said membrane being a polycarbonate membrane.

3. A method for manufacturing a membrane according to claim 1, comprising providing a monolayer membrane for cell culture, comprising a first type of pore having an average diameter between 0.1 and 1 µm, at a density of $1 \times 10^5$ to $1 \times 10^8$ pores per $cm^2$ of membrane; and perforating said monolayer membrane in such a way as to produce a second type of pore that has an average diameter between 2 and 12 µm, at a density of $0.5 \times 10^2$ to $5 \times 10^3$ pores per $cm^2$ of membrane.

4. The method of manufacturing according to claim 3, wherein the membrane is perforated by laser perforation.

5. A cell culture device comprising at least one compartment of which at least one of the walls comprises or is constituted by a membrane according to claim 1.

6. The device according to claim 5, said device comprising two compartments and said wall comprising or being constituted by said monolayer membrane separating the two compartments.

7. A method for manufacturing a cell culture device according to claim 5, comprising providing a cell culture device for cell culture, which comprises at least one compartment of which at least one of the walls comprises or is constituted by a monolayer membrane which comprises a first type of pore having an average diameter between 0.1 and 1 µm, at a density of $1 \times 10^5$ to $1 \times 10^8$ pores per $cm^2$ of membrane; and
perforating said monolayer membrane in such a way as to produce a second type of pore that has an average diameter between 2 and 12 µm, at a density of $0.5 \times 10^2$ to $5 \times 10^3$ pores per $cm^2$ of membrane.

8. A method for the preparation of a reconstructed biological tissue comprising at least two cell types, which comprises:
   a1) seeding a first cell type of the tissue to be reconstructed in a at least one compartment of the culture device according to claim 5 in such a way as to allow for adhesion of the first cells to the membrane of the culture device,
   a2) after a period required to allow for the adhesion of the first cells to the membrane of the culture device, and
   b) maintaining the first and cells of a second type in culture for a period and in conditions suitable for enabling the characteristic cellular organization of the tissue.

9. A reconstructed biological tissue comprising at least one group of cells (i) comprising at least one first cell type on a monolayer membrane according to claim 1.

10. A method for preparing a reconstructed biological tissue comprising at least one cell type, in a cell culture device according to claim 5, comprising the following steps:
   a) seeding a first cell type of the tissue to be reconstructed in said at least one compartment of the culture device, in such a way as to allow for its adhesion to the membrane of the culture device, and
   b) maintaining the cells in culture for a period and in conditions suitable for enabling the characteristic cellular organization of the tissue.

11. A method for manufacturing a membrane according to claim 2 comprising providing a monolayer polycarbonate membrane for cell culture, comprising a first type of pore having an average diameter between 0.1 and 1 µm, at a density of $1 \times 10^5$ to $1 \times 10^8$ pores per $cm^2$ of membrane, and perforating said monolayer membrane in such a way as to produce a second type of pore that has an average diameter between 2 and 12 µm, at a density of $0.5 \times 10^2$ to $5 \times 10^3$ pores per $cm^2$ of membrane.

12. A cell culture device comprising at least one compartment of which at least one of the walls comprises or is constituted by a membrane according to claim 2.

13. A method for manufacturing a cell culture device according to claim 6, comprising providing a cell culture device for cell culture, which comprises two compartments separated by a wall, wherein the wall comprises or is constituted by a monolayer membrane which comprises a first type of pore having an average diameter between 0.1 and 1 µm, at a density of $1 \times 10^5$ to $1 \times 10^8$ pores per $cm^2$ of membrane; and
perforating said monolayer membrane in such a way as to produce a second type of pore that has an average diameter between 2 and 12 µm, at a density of $0.5 \times 10^2$ to $5 \times 10^3$ pores per $cm^2$ of membrane.

14. A method for the preparation of a reconstructed biological tissue comprising at least two cell types, which comprises:
   a1) seeding a first cell type of the tissue to be reconstructed in a compartment of the culture device according to claim 6 in such a way as to allow for adhesion of the first cells to the membrane of the culture device,
   a2) after a period required to allow for the adhesion of the first cells to the membrane of the culture device, seeding the second cell type in the other of said two compartments of the cell culture device according to claim 6, and
   b) maintaining the first and second cells in culture for a period and in conditions suitable for enabling the characteristic cellular organization of the tissue.

\* \* \* \* \*